United States Patent [19]

Relles et al.

[11] 4,247,464

[45] Jan. 27, 1981

[54] LIQUID EXTRACTION METHOD FOR RECOVERING AROMATIC BISIMIDES

[75] Inventors: Howard M. Relles, Rexford; Frank J. Williams, III, Scotia, both of N.Y.

[73] Assignee: General Electric Company, Schenectady, N.Y.

[21] Appl. No.: 80,541

[22] Filed: Oct. 1, 1979

[51] Int. Cl.³ .............................................. C07D 209/48
[52] U.S. Cl. .............................. 260/326 N; 260/326 S
[58] Field of Search .......... 260/326 A, 326 N, 326 R, 260/326 S; 568/723, 724

[56] References Cited

U.S. PATENT DOCUMENTS

| | | | |
|---|---|---|---|
| 3,852,242 | 12/1974 | White | 260/47 CZ |
| 3,957,862 | 5/1976 | Heath et al. | 260/346.3 |
| 4,048,190 | 9/1977 | Johnson et al. | 260/326 N |
| 4,054,577 | 10/1977 | Relles et al. | 260/326 S |

OTHER PUBLICATIONS

Grant, Hacklis Chem. Dictionary, McGraw-Hill, 1969, p. 640.
C. Starks, JACS 93:1 (1971), pp. 195-199.
D. Landini et al., Synthesis, 389, (1976).

Primary Examiner—Donald G. Daus
Assistant Examiner—M. C. Eakin
Attorney, Agent, or Firm—William A. Teoli; James C. Davis, Jr.

[57] ABSTRACT

A liquid extraction method is provided for recovering aromatic bisimides from an organic solvent aromatic bisimide reaction mixture having a variety of reaction by-products. An organic solvent solution of the bisimide reaction mixture is extracted with water and/or an aqueous alkali metal hydroxide to effect removal of such reaction by-products, and provide an organic solvent phase of the aromatic bisimide which can be obtained in substantially pure form upon removal of the organic solvent.

6 Claims, No Drawings

LIQUID EXTRACTION METHOD FOR RECOVERING AROMATIC BISIMIDES

CROSS REFERENCE TO RELATED APPLICATIONS

Reference is made to copending application Ser. No. 037,441, filed May 9, 1979 of Frank J. Williams, III, for Method for Making Aromatic Ether Imides and Ser. No. 037,442, filed May 9, 1979 of Frank J. Williams, III et al, for Method for Making Alkali Metal Bisphenoxide Salts and Bisimides Derived Therefrom, both applications being assigned to the same assignee as the present invention.

BACKGROUND OF THE INVENTION

The present invention relates to an extraction method for recovering aromatic bisimide from an aromatic bisimide reaction mixture. An organic solvent solution of aromatic bisimide reaction solids is extracted with water and/or extracted with an aqueous alkali metal hydroxide.

Prior to the present invention, a method for making aromatic bisimides of the formula,

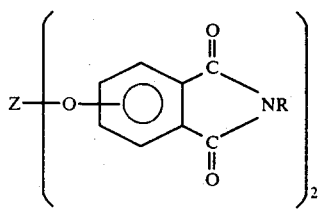

was based on the reaction of a substituted N-organo phthalimide and an alkali bisphenoxide in a dipolar aprotic solvent, where R is a monovalent $C_{(1-13)}$ organic radical and Z is a $C_{(6-30)}$ divalent aromatic organic radical. The resulting reaction mixture contained in addition to the aromatic bisimide of formula (1), a variety of reaction solids including phenolic monoimide of the formula,

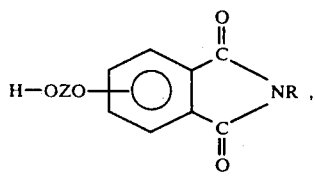

alkali metal substituted phthalic salts of the formula,

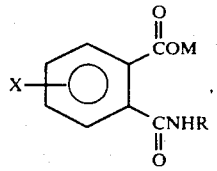

where X is selected from a nitro or halo radical and M is an ion of an alkali metal, unreacted substituted N-alkyl phthalimide of the formula,

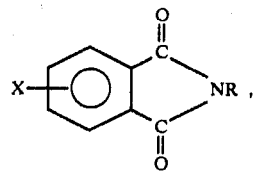

and alkali metal bisphenoxide salts of the formula, $$Z\text{-}(OM)_2. \quad (5)$$

in addition, there also was included in the reaction mixture alkali metal nitrites and substituted phthalic acid amides of the formula,

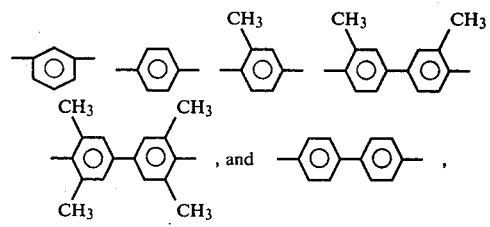

where R and Z are as previously defined.

Radicals included by Z of formula (1), are for example,

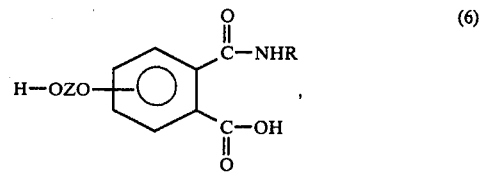

and divalent organic radicals of the general formula,

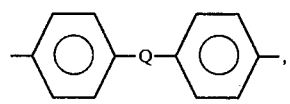

where Q is a member selected from the class consisting of divalent radicals of the formulas,

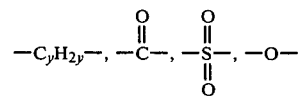

and —S— and y is an integer from 1 to 5. Monovalent organic radicals included within R are, for example, $C_{(6-13)}$ aromatic hydrocarbon radicals, $C_{(1-8)}$ aliphatic radicals and halogenated derivatives thereof, for example, methyl, ethyl, propyl, heptyl, octyl, chloroethyl, etc.; phenyl, tolyl, xylyl, naphthyl, anthryl, etc.; cycloalkylene radicals having from 3 to about 12 carbon atoms, etc.

M of formula (2) can include alkali metal ions, for example, sodium, potassium, etc., and X is a monovalent radical selected from nitro, and halo radicals, for example, chloro, fluoro, bromo, etc.

The procedures of the prior art used to isolate the aromatic bisimide of formula (1) from the aforementioned impurities were generally based on recovering the reaction mixture as a crystalline solid and further treating the solid with an appropriate solvent, grinding the solvent-solid mixture, filtering, further grinding with solvent, etc.

As shown in copending applications Ser. Nos. 37,441 and 37,442 of Frank J. Williams et al filed May 9, 1979, improved solids handling results can be achieved with respect to recovering the aromatic bisimide of formula (1) in substantially pure form by substituting a non-polar organic solvent, such as toluene, in combination with a phase transfer catalyst for the dipolar aprotic solvent of the prior art. Unlike the solid handling procedures required in isolating the aromatic bisimide when using a dipolar aprotic solvent, the phase transfer catalyst allows for the production of a non-polar organic solvent solution of the aromatic bisimide and other reaction solids which can be readily separated therefrom with a precipitating organic solvent such as methanol. However, experience has shown that such precipitating solvents often do not satisfactorily remove particular reaction components, such as the unreacted N-alkyl-nitrophthalimide of formula (4). In addition, the use of such precipitating solvents are often uneconomic and can have an adverse environmental impact.

The present invention is based on the discovery that aromatic bisimide of formula (1), can be recovered free of contaminating solids of formulas (2–6), without an extensive solids handling procedure, by treating a solution of the aromatic bisimide reaction mixture with water and/or an aqueous solution of an alkali metal hydroxide. In the event a water soluble dipolar aprotic organic solvent is initially used in the reaction mixture, a substantially water insoluble organic solvent, for example, methylene chloride, can be used prior to the aqueous wash and/or aqueous base treatment to prevent premature separation of reaction solids.

STATEMENT OF THE INVENTION

There is provided by the present invention, a method for making aromatic bisimides of formula (1), comprising the reaction of alkali metal bisphenoxide of formula (5) and substituted phthalimide of formula (4), where there is used about 2 moles of the substituted phthalimide per mole of the alkali metal bisphenoxide, which reaction is conducted in the presence of an organic solvent selected from (A) a dipolar aprotic organic solvent, or (B) a non-polar organic solvent and a phase transfer catalyst, to produce either a dipolar organic solvent reaction mixture with (A) requiring a multi-step purification procedure involving the handling of reaction solids, or a non-polar organic solvent solution with (B) requiring the use of a precipitating organic solvent to effect the removal of certain components from the reaction mixture, which comprises the improvement of (1) adding an organic solvent to the dipolar aprotic organic solvent reaction mixture of (A) and extracting the resulting solution with water to produce an organic solvent of aromatic bisimide substantially free of dipolar organic solvent and/or (2) treating the organic solvent solution with an aqueous solution of an alkali metal hydroxide to produce a volatile organic solvent solution of substantially pure aromatic bisimide, and (3) stripping the volatile organic solvent from the mixture of (2).

Some of the bisimides of formula (1) are shown in Heath et al U.S. Pat. No. 3,879,428 and include, for example, 2,2-bis-[4-(N-phenylphthalimide-3-oxy)-phenyl]propane, 2,2-bis[4-(N-phenylphthalimide-4-oxy)phenyl]propane, 1,4-bis(N-phenylphthalimide-3-oxy)benzene, etc.

Substituted N-organic phthalimides of formula (4) are, for example, N-phenyl-3-nitrophthalimide, N-phenyl-4-nitrophthalimide, N-methyl-3-nitrophthalimide, N-butyl-4-nitrophthalimide, etc. The substituted phthalimides of formula (4) are, for example, nitrophthalimides, can be made by effecting reaction between substantially equal mols of nitrophthalic anhydride or halophthalic anhydride and an organic amine, for example, methyl amine, ethyl amine, aniline, toluidene, etc., in the presence of refluxing acetic acid.

There are included by the alkali metal salts of the above-described alkali diphenoxides of formula (2), sodium and potassium salts of the following dihydric phenols:

2,2-bis(2-hydroxyphenyl)propane;
2,4'-dihydroxydiphenylmethane;
bis-(2-hydroxyphenyl)methane;
2,2-bis-(4-hydroxyphenyl)propane; hereinafter identified as "bisphenol-A; or "BPA";
1,1-bis-(4-hydroxyphenyl)ethane;
1,1-bis-(4-hydroxyphenyl)proapne;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxybenzophenone; and
4,4'-dihydroxydiphenylether.

In the practice of the invention, aromatic bisimide reaction mixture resulting from the reaction of alkali metal bisphenoxide of formula (5), and substituted N-alkylphthalimide of formula (4) is treated in the presence of organic solvent at temperatures of 25° C. to 150° C. with an aqueous alkali metal hydroxide to effect removal of various reaction components, as shown by formulas 2–6, from the aromatic bisimide which remains in the organic phase.

In instances where the aromatic bisimide is formed in the presence of a dipolar aprotic solvent, it must be removed prior to the base treatment to minimize dipolar aprotic solvent breakdown and the generation of deleterious organic amines which lead to additional undesired by-products. Suitable dipolar aprotic organic solvents are, for example, N,N-dimethylformamide, N-methylpyrrolidone, N,N-dimethylacetamide, dimethylsulfoxide, etc.

Prior to the removal of the dipolar aprotic solvent from the reaction mixture, which can be readily achieved by a washing step, a solubilizing organic solvent can be added to avoid precipitation of reaction solids. Suitable solubilizing organic solvents are, for example, methylene chloride, 1,2-dichloroethane, chloroform, etc. In certain instances, non-polar azeotroping solvents can be used in combination with the dipolar aprotic solvent as an azeotropic solvent and include, for example, toluene, benzene, etc.

The initial reaction mixture can contain from 5 to 50% solids, based on the total weight of reaction mixture. After a solubilizing organic solvent has been added to the mixture, the mixture can be washed at least 1 to 10 times with 0.25 to 10 volumes of water, per volume of mixture to effect the removal of the dipolar aprotic solvent and inorganic salts. The organic phase is then extracted with an aqueous alkali metal hydroxide solution having 0.2% to 10% by weight of alkali metal hydroxide. The resulting organic phase can then be dried with magnesium sulfate, filtered and stripped of the solubilizing organic solvent to produce the aromatic bisimide.

In instances where the aromatic bisimide is made using a non-polar organic solvent, there is used in combination with the non-polar organic solvent an effective amount of phase transfer catalyst, i.e., from 0.005 equivalent to 2 equivalents of catalyst per equivalent of alkali bisphenoxide of formula (5) and preferably from 0.02 to 0.5 equivalent. Phase transfer catalyst which can be used is included within the formula, $(R^2)_4Q^1Y$, (7)

where $R^2$ is selected from $C_{(1-16)}$ alkyl radicals and $C_{(6-13)}$ aromatic radicals, $Q^1$ is a Group Va element selected from N and P, and Y is a halogen or carboxy radical. Included within the phase transfer catalysts of formula (7) are, for example, tetra butylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium bromide, tetrabutylphosphonium chloride, etc.

It has been found that the need for a solubilizing organic solvent can be eliminated if the non-polar organic solvent-phase transfer catalyst reaction mixture is maintained at a temperature of 70° C. to 220° C. The resulting organic solvent solution can be treated with the aqueous alkali-metal hydroxide solution, to produce upon drying, a non-polar organic solvent solution of the aromatic bisimide. Recovery of the desired aromatic bisimide from the resulting solution can thereafter be achieved by stripping the non-polar organic solvent under reduced pressure.

In order that those skilled in the art will be better able to practice the invention, the following examples are given by way of illustration and not by way of limitation. All parts are by weight.

EXAMPLE 1

A suspension of 0.5098 part of the disodium salt of bisphenol-A, prepared by complete removal of methanol from the corresponding solution of the salt, having a purity of 98.7% and 0.7798 part of 4-nitro-N-methylphthalimide in 9.4 parts of anhydrous dimethylformamide was stirred at a temperature of 70°-72° C. under nitrogen for 1 hour. The mixture was analyzed by high pressure liquid chromatography using a Water Associates Micro C-18 Reverse Phase column and solvent programming using a 90:10-acetonitrile-methanol mixture and water.

A sample of the reaction mixture was diluted with an equal volume of methylene chloride and then extracted four times with water, reanalyzed by HPLC and then extracted seven times with 10% aqueous sodium hydroxide with additional HPLC analysis during these extractions. The following results were obtained as shown in Table I below, where 4,4-BPA-BI is shown by formula (1) and is the corresponding bis-N-methylphthalimide of bisphenol-A (i.e.: 2,2-bis[4-(3,4-dicarboxyphenoxy)phenyl]propane-bis-N-methylimide), 4-BPA-MI is shown by formula (2) as the corresponding mono-M-methylphthalimide of bisphenol-A, 4-NPI is shown by formula (4) as the corresponding 4-nitro-N-methylphthalimide, PI is N-methylphthalimide and 4-NO$_2$-A-A is shown by formula (3).

TABLE I

| Compound | 1 hour Reaction Mixture | Methylene Chloride Dilute Mixture | | | |
|---|---|---|---|---|---|
| | | 4 × H$_2$O extractions | 1 × NaOH extractions | 4 × NaOH extractions | 7 × NaOH extractions |
| 4,4-BPA-BI | 96.99 | 97.07 | 97.07 | 97.07 | 97.07 |
| 3,4-BPA-BI | 1.12 | 1.10 | 1.11 | 1.07 | 1.06 |
| 4-BPA-MI | 1.80 | 1.74 | 0.99 | 0 | 0 |
| BPA | 0.08 | 0.08 | 0 | 0 | 0 |
| 4-NPI | 1.33 | 1.18 | 0.35 | 0.03 | 0 |
| PI | 0.14 | 0.14 | 0.05 | 0 | 0 |
| 4-NO$_2$-A.A. | (TRACE) | 0 | 0 | 0 | 0 |

The above results show that total removal of all impurities were achieved without creating additional impurities.

EXAMPLE 2

A mixture of 1.2007 part of the disodium salt of bisphenol-A, 1.8366 part of 4-nitro-N-methylphthalimide, 0.8275 part of benzophenone and 18.8 parts of anhydrous dimethylformamide, were combined and stirred under nitrogen at 70°-72° C. for a total of 240 minutes. Samples of the reaction mixture were withdrawn and analyzed by high pressure liquid chromatography after 30 minutes at 60 minutes. Another 60 minute sample was diluted with methylene chloride and put through an extractive workup in which the system was treated with aqueous sodium hydroxide before all of the dimethylformamide had been thoroughly removed by water extraction. As a result, by-products such as diamideimide and the tetra-amide were generated from the hydrolysis product of the solvent: dimethylamine.

Another sample of 240 minute reaction mixture was then analyzed after thorough water extraction. The benzophenone was employed as an internal standard. It was found that the distribution and amounts of product were virtually unaffected by the water extraction, except that 4-nitro-amide acid (3) was completely removed along with sodium nitrite and dimethylformamide. The extraction with 10% aqueous sodium hydroxide was found to effectively remove not only the phenolic 4-bisphenol-A methyl imide (2) and bisphenol-A (5), but also, surprisingly, the 4-nitro-N-methylphthalimide and N-methyl-phthalimide. At the same time, there was no formation of the diamide-imide or the tetra-amide impurities. The results obtained are shown in Table II, where the terms used are as previously defined in Example 1, except for the diamide-imide and tetra-amide reaction by-products.

yield of 4,4-bisphenol-A-bisphthalimide which was 100% pure based on liquid chromatography.

Although the above examples are directed to only a few of the very many variables within the scope of the present invention, it should be understood that the present invention is directed to a much broader procedure for recovering aromatic bisimides as shown by formula (1), based on the use of a solution of an alkali metal hydroxide with an organic solvent solution of the aro-

TABLE II

| | | | Methylene Chloride Diluted Mixtures | | |
|---|---|---|---|---|---|
| | Reaction Mixture | | 4 × H₂O extraction (of 240 min Rx. Mixt.) | 1 × H₂O extr., 4 × 10%-NaOH extr., and 1 × H₂O extra. (of 60 min Rx. Mixt.) | 4 × H₂O extr., and 5 × 10%-NaOH extr. (of 240 min Rx. Mixt.) |
| Compound | 30 min | 60 min | | | |
| 4,4-BPA-BI | 97.01 | 97.40 | 97.44 | 80.94 | 97.44 |
| 3,4-BPA-BI | 1.09 | 1.10 | 1.09 | 0.91 | 1.09 |
| 4-BPA-MI | 1.60 | 1.32 | 1.30 | 0 | 0 |
| BPA | 0.30 | 0.18 | 0.17 | 0 | 0 |
| 4-NPI | 1.81 | 1.30 | 1.12 | 0 | 0.03 |
| PI | 0.16 | 0.14 | 0.14 | 0 | 0 |
| 4-NO₂-A.A. | (TRACE) | (TRACE) | 0 | 0 | 0 |
| Diamide-imide | 0 | 0 | 0 | 15.70* | 0 |
| tetra-amide | 0 | 0 | 0 | 0.96* | 0 |

*Approximate values (± 5%)

EXAMPLE 3

A mixture of 20.6 parts of bisphenol-A, 38.9 parts of 4-nitro phthalimide, 7.98 parts of sodium hydroxide pellets, 101 parts of dimethyl formamide, and 56 parts of toluene was refluxed under nitrogen for 8 hours. During the course of the reaction, water was azeotropically removed under reduced pressure. The reaction mixture was then diluted with about 550 parts of methylene chloride. The mixture was then filtered to remove solids and about 5 parts of acetic acid was added to it. The mixture was then extracted with 4×500 parts of water and about 3×500 parts of a 5% sodium hydroxide solution and about 1×500 parts of a saturated sodium chloride solution. The organic phase was then dried and concentrated to give 40 parts of the 4,4'-bisphenol-A bisimide which contained a trace amount, i.e. 0.6% of the 4-nitro-phthalimide.

EXAMPLE 4

The homogenous solution of 20 parts of bisphenol-A and 7.0011 parts of sodium hydroxide was prepared in 41 parts of water upon warming to 80°-90° C. There was then added approximately 86 parts of toluene and the system was azeotropically dried. Water was totally removed over a period of 2-3 hours. The mixture was then distilled until there remained about 38 parts of toluene in the resulting suspension. The suspension was allowed to cool a few degrees so that refluxing ceased. There was then added 36.15 parts of 4-nitro-phthalimide and 0.71 part of tetrabutylammonium bromide. The suspension was brought back to reflux where it was maintained for one hour. The resulting mixture was then found to contain 95.5% of 4,4-bisphenol-A bisimide, 1.3% by weight of 3,4-bisphenol-A-bisimide, 0.8% of 4-bisphenol-A-N-methylphthalimide, and 2.3% by weight of 4-nitro-N-methylphthalimide. The analysis was obtained by liquid chromatography. The mixture was then diluted with about 78 parts of toluene and extracted with 150 parts of a 1% aqueous sodium hydroxide solution at 70°-75° C. The organic layer was then stripped with solvent. There was obtained a 94% matic bisimide.

What we claim as new and desire to secure by Letters Patent of the United States is:

1. A method of making an aromatic bisimide of the formula,

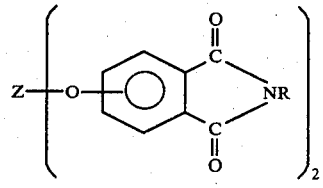

which comprises
(1) effecting the reaction of an alkali metal bisphenoxide of the formula,

Z+OM)₂, and a substituted phthalimide of the formula,

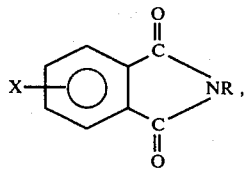

in the presence of a dipolar aprotic organic solvent, where there is used about 2 moles of the substituted phthalimide, per mole of the alkali metal bisphenoxide,
(2) adding a solubilizing organic solvent to the dipolar aprotic organic solvent reaction mixture of (1), and extracting the resulting mixture with water to produce an organic solvent phase free of the dipolar aprotic solvent,
(3) treating the solubilizing organic solvent phase of (2) with an aqueous solution of an alkali metal hydroxide and (4) stripping the resulting organic solvent solution of (3) to recover the aromatic bisimide, where Z is a $C_{(6-30)}$ divalent aromatic organic radical, R is a monovalent $C_{(1-13)}$ organic radical, X is selected from a nitro or halo radical, and M is an ion of an alkali metal.

2. A method for making aromatic bisimide of the formula,

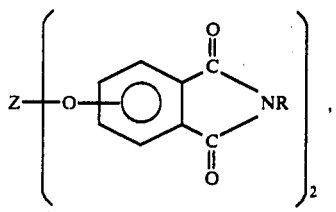

which comprises (1) effecting reaction between an alkali metal bisphenoxide of the formula,

and a substituted phthalimide of the formula,

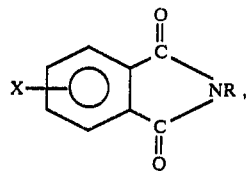

in the presence of a nonpolar organic solvent and a phase transfer catalyst, where there is used about 2 moles of the substituted phthalimide, per mole of the alkali metal bisphenoxide (2) treating the resulting nonpolar organic solvent solution with an aqueous solution of an alkali metal hydroxide and (3) stripping the organic solvent from the resulting mixture of (2) to effect the recovery of the aromatic bisimide, where Z is a $C_{(6-30)}$ divalent aromatic organic radical, R is a monovalent $C_{(1-13)}$ organic radical, X is selected from nitro or halo radical, and M is an ion of an alkali metal.

3. A method in accordance with claim 1, where methylene chloride is added to the dipolar aprotic solvent prior to extracting the reaction mixture with water.

4. A method in accordance with claim 1, where the aromatic bisimide is 4,4'-bisphenol-A-bis-N-methylphthalimide.

5. A method in accordance with claim 2, where the nonpolar organic solvent is toluene.

6. A method in accordance with claim 2, where the phase transfer catalyst is tetrabutyl ammonium bromide.

* * * * *